US008855384B2

(12) United States Patent
Kyal et al.

(10) Patent No.: US 8,855,384 B2
(45) Date of Patent: Oct. 7, 2014

(54) CONTINUOUS CARDIAC PULSE RATE ESTIMATION FROM MULTI-CHANNEL SOURCE VIDEO DATA

(75) Inventors: Survi Kyal, Rochester, NY (US); Lalit Keshav Mestha, Fairport, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 248 days.

(21) Appl. No.: 13/528,307

(22) Filed: Jun. 20, 2012

(65) Prior Publication Data
US 2013/0343614 A1    Dec. 26, 2013

(51) Int. Cl.
*G06K 9/00*    (2006.01)

(52) U.S. Cl.
USPC .......................................... 382/128; 382/107

(58) Field of Classification Search
USPC .......................................................... 382/128
See application file for complete search history.

(56) References Cited

U.S. PATENT DOCUMENTS

| | | | |
|---|---|---|---|
| 6,934,578 B2* | 8/2005 | Ramseth | 600/523 |
| 2003/0161527 A1* | 8/2003 | Wang | 382/156 |
| 2009/0072824 A1* | 3/2009 | Romero | 324/303 |
| 2011/0251493 A1 | 10/2011 | Poh et al. | |
| 2013/0290011 A1* | 10/2013 | Lynn et al. | 705/2 |
| 2013/0296660 A1* | 11/2013 | Tsien et al. | 600/301 |

OTHER PUBLICATIONS

Wei Lu et al., "Approach and Applications of Constrained ICA", IEEE Transactions on Neural Networks, vol. 16, No. 1, Jan. 2005.
Wei Lu et al., "Constrained Independent Component Analysis", School of Computer Engineering, Nanyang Technological University, Singapore 639798, 2000.
Takano et al., "Heart rate measurement based on a time-lapse image", Medical Engineering & Physics 29 (2007), pp. 853-857, www.sciencedirect.com.
Poh et al., "Non-contact, automated cardiac pulse measurements using video imaging and blind source separation.", May 10, 2010, vol. 18, No. 10 / Optics Express 10762.
Lee et al., "Temporally constrained ICA-based foetal ECG separation", Electronics Letters, Oct. 13, 2005, vol. 41, No. 21.
Mestha et al., "Systems and Methods for Non-Contact Heart Rate Sensing", U.S. Appl. No. 13/247,575, filed Sep. 28, 2011.
Xu et al., "A Multi-Layer Array for a Multi-Resolution Multi-Spectral Camera," U.S. Appl. No. 13/239,642, filed Sep. 22, 2011.

(Continued)

*Primary Examiner* — Utpal Shah
(74) *Attorney, Agent, or Firm* — Philip E. Blair; Fleit Gibbons Gutman Bongini & Bianco P.L.

(57) ABSTRACT

What is disclosed is a computationally efficient system and method for estimating a subject's cardiac pulse rate from multi-channel source video data. In one embodiment, A time-series signal is received. A sliding window is used to define overlapping segments of the time-series signal. Signal segments are processed by performing constrained independent component analysis (cICA) until convergence to obtain an estimated source signal. A frequency of each estimated source signal obtained by the cICA at convergence is determined to be the subject's estimated cardiac pulse rate for each signal segment. A seed reference signal used by the cICA is repeatedly updated. A sliding window is shifted to define a next time-series signal segment for processing. The method repeats for each signal segment until a termination criteria is met. In such a manner, the subject's cardiac pulse rate is estimated from a video of the subject on a continuous basis.

24 Claims, 14 Drawing Sheets

(56) References Cited

OTHER PUBLICATIONS

Yang et al., "Vital Sign Estimation from Passive Thermal Video," IEEE Conference on Computer Vision and Pattern Recognition, Jun. 2008, pp. 23-28.
Garbey et al., "Contact-Free Measurement of Cardiac Pulse Based on the Analysis of Thermal Imagery," IEEE Transactions on Biomedical Engineering, Aug. 2007, vol. 54, No. 8, pp. 2-13.
Mestha et al., "Method for Classifying a Pixel of a Hyperspectral Image in a Remote Sensing Application," U.S. Appl. No. 13/023,310, filed Feb. 8, 2011.
Wang et al., "Determining a Total Number of People in a IR Image Obtained Via an IR Imaging System," U.S. Appl. No. 12/967,775, filed Dec. 14, 2010.
Xu et al., "System and Method for Object Identification and Tracking," U.S. Appl. No. 13/247,343, filed Sep. 28, 2011.
Lee et al., "Speech Coding and Noise Reduction Using Ice-Based Speech Features," in P. Pajunen and J. Karhunen (eds.), Proc. Second International Workshop on Independent Component and Analysis and Blind Signal Separation, 2000.
Hoyer et al., "ICA Features of Colour and Stereo Images," P. Pajunen and J. Karhunen (eds.), Proc. Second International Workshop on Independent Component and Analysis and Blind Signal Separation, 2000, pp. 567-572.
Bell et al., "The "Independent Components" of Natural Science are Edge Filters," Vision Ref., 1997, vol. 37, No. 23, pp. 3327-3338.
Lee et al., "Application of independent component analysis to microarrays," Genome Biology, 2003, vol. 4, Issue 11, R76.
Cantelli, Mark, "Are you in There?" Tolltrans 2011, www.TrafficTechnologyToday.com.
Mestha, et al., "Estimating Cardiac Pulse Recovery From Multi-Channel Source Data Via Constrained Source Separation", U.S. Appl. No. 13/247,683, filed Sep. 28, 2011.
Mestha et al., "Filtering Source Video Data Via Independent Component Selection", U.S. Appl. No. 13/281,975, filed Nov. 8, 2011.
Cardoso, Jean-Francois, "Blind signal separation: statistical principles", pp. 1-16, (Official Version published as: Proceedings of the IEEE, vol. 9, No. 10, pp. 2009-2025, Oct. 1998).
Hyvarinen et al., "Independent Component Analysis: Algorithms and Applications", Neural Networks Research Centre, Helsinki University of Technology, Finland, Neutral Networks, pp. 1-31, 13(4-5); 411-430, 2000.
Wang et al., "Determining a Number of Objects in an IR Image", U.S. Appl. No. 13/086,006, filed Apr. 28, 2011.
Wang, et al., "Post-Processing a Multi-Spectral Image for Enhanced Object Identification", U.S. Appl. No. 13/324,368, filed Dec. 28, 2011.
Mestha et al., "Removing Environment Factors From Video Signals Captured for Biomedical Measurements", U.S. Appl. No. 13/401,207, filed Feb. 21, 2012.
Pressman et al., "A Transducer for the Continuous External Measurement of Arterial Blood Pressure", External Measurement of Blood Pressure, IEEE Transactions on Bio-Medical Electronics, Apr. 1963, pp. 73-81.
Meigas et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.
Penaz, J., "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.
Aubert et al., "A Model-Based Study of the Influence of Vaso-Active Drugs on Pulse Delays Measured from the Electrocardiogram", Computers in Cardiology 2007:34:383-386.
Naschitz et al., "Pulse Transit Time by R-Wave-Gated Infrared Photoplethysmography: Review of the Literature and Personal Experience", Journal of Clinical Monitoring and Computing (2004) 18: 333-342, Springer 2005.
Reisner et al., "Utility of the Photoplethysmogram in Circulatory Monitoring", Anesthesiology, vol. 108, No. 5, May 2008, pp. 950-958.
Dalal et al., "Histograms of Oriented Gradients for Human Detection", Proceedings of the Conference on Computer Vision and Pattern Recognition, San Diego, California, USA, pp. 886-893, (2005).
Skaff et al., "Estimating a Visible Vector Representation for Pixels in an Infrared Image", U.S. Appl. No. 13/364,835, filed Feb. 2, 2012.
Xu et al., "Subcutaneous Vein Pattern Detection Via Multi-Spectral IR Imaging in an Identity Verification System", U.S. Appl. No. 13/087,850, filed Apr. 15, 2011.
Mestha et al., "Deriving Arterial Pulse Transit Time From a Source Video Image", U.S. Appl. No. 13/401,286, filed Feb. 21, 2012.
Piratla et al., "Web-Based System and Method for Video Analysis", U.S. Appl. No. 13/417,979, filed Mar. 12, 2012.
Xu et al., "Monitoring Respiration With a Thermal Imaging System", U.S. Appl. No. 13/103,406, filed May 9, 2011.
Wang et al., "Multi-Band Infrared Camera System Optimized for Skin Detection", U.S. Appl. No. 13/416,436, filed Mar. 9, 2012.

\* cited by examiner

CONTINUOUS CARDIAC PULSE RATE ESTIMATION FROM MULTI-CHANNEL SOURCE VIDEO DATA

TECHNICAL FIELD

The present invention is directed to systems and methods for continuously estimating cardiac pulse rate from multi-channel source video data captured of a patient being monitored for cardiac function.

BACKGROUND

A normal heart rate for healthy adults, during rest can range from 60 to 100 beats per minute (bpm) but can drop to 40 bpm during sleep and go as high as 240 bpm during vigorous exercise. One commonly used maximum heart rate formula is: Max HR=220 minus Age. Clearly, for infants and premature babies, their heart rates are quite high. Our previous patent application: "Systems And Methods For Non-Contact Heart Rate Sensing", U.S. patent application Ser. No. 13/247,575, by Mestha et al., disclosed a method for analyzing a video to determine a subject's heart rate. For large patient populations and various living conditions, this heart rate algorithm may have to step through 40 bpm to an ultimate maximum of 240 bpm in at least one beat per minute intervals. While sweeping through 1 bpm steps, there is a single frequency (very close to the true pulse) for which the error is very close to zero. FIG. 1 shows an error plot with one infant video between an input heart rate to an extracted heart rate using the previously disclosed method for a limited range of 120 to 240 bpm. Because one needs to step through as many as 180 intervals per batch to achieve a resolution of 1 bpm, this can be computationally intensive when such operations have to be performed repeatedly for every new batch of new data during continuous monitoring. What is desirable is a method for computing a subject's cardiac pulse across a large range, i.e., from about 40 bpm to 240 bpm, in at least one beat per minute intervals, in a computationally efficient manner for continuous monitoring or when a large number of sequential segments have to be processed.

Accordingly, what is needed in this art is a computationally efficient system and method for estimating a subject's cardiac pulse rate from multi-channel source video data that can be used in a continuous monitoring mode with a high degree of measurement accuracy.

INCORPORATED REFERENCES

The following U.S. Patents, U.S. Patent Applications, and Publications are incorporated herein in their entirety by reference.

"Estimating Cardiac Pulse Recovery From Multi-Channel Source Data Via Constrained Source Separation", U.S. patent application Ser. No. 13/247,683, by Mestha et al.

"Systems And Methods For Non-Contact Heart Rate Sensing", U.S. patent application Ser. No. 13/247,575, by Mestha et al.

"Filtering Source Video Data Via Independent Component Selection", U.S. patent application Ser. No. 13/281,975, by Mestha et al.

"Removing Environment Factors From Signals Generated From Video Images Captured For Biomedical Measurements", U.S. patent application Ser. No. 13/401,207, by Mestha et al.

"Web-based system and method for video analysis", U.S. patent application Ser. No. 13/417,979, by Piratla et al.

"Deriving Arterial Pulse Transit Time From A Source Video Image", U.S. patent application Ser. No. 13/401,286, by Mestha.

"Approach and Applications of Constrained ICA", Wei Lu and Jagath C. Rajapakse, IEEE Transactions On Neural Networks, Vol. 16, No. 1, pp. 203-212, (January 2005).

"Independent Component Analysis", Aapo Hyvärinen, Juha Karhunen, and Erkki Oja, Wiley-Interscience, $1^{st}$ Ed. (2001), ISBN-13: 978-0471405405.

"Independent Component Analysis: Principles and Practice", Stephen Roberts (Editor), Richard Everson (Editor), Cambridge University Press; $1^{st}$ Ed. (2001), ISBN-13: 978-0521792981.

BRIEF SUMMARY

What is disclosed is a computationally efficient system and method for estimating a subject's cardiac pulse rate from multi-channel source video data that can be used in a continuous monitoring mode with a high degree of measurement accuracy. The system and methods disclosed herein find their uses in a variety of diverse applications such as, for instance, in telemedicine, emergency rooms, cardiac intensive care units, neonatal intensive care units (NICUs), including military and security applications.

One embodiment of the present method for continuous cardiac pulse estimation from video images captured of a subject of interest being monitored for cardiac function in a remote sensing environment, involves the following. A time-series signal is received which is being actively acquired. The time-series signal is continuously segmented using a sliding window such that each position of the window defines overlapping successive signal segments for processing. For each signal segment, as defined by the sliding window, constrained independent component analysis (cICA) is repeatedly performed on each signal segment until convergence, (i.e., an error between the signal segment and the reference signal is less than a threshold), or a defined number of iterations have occurred. If the error is less than the threshold, a frequency of the estimated source signal at the time of convergence is determined to be the subject's estimated cardiac pulse rate corresponding to this signal segment. This estimated source signal is then conditioned to remove unwanted artifacts and becomes the reference signal to be used by the cICA algorithm for processing the next time-series signal segment on a next iteration. If, on the other hand, the cICA failed to converge, (i.e., a defined number of iterations occurred) then the reference signal used by the cICA algorithm to process this time-series signal segment is updated by changing any of: a frequency, an amplitude, a phase, or a waveform of the reference signal and the updated reference signal is used to re-process the current signal segment. Alternatively, an estimated source signal obtained from having processed a previous time-series signal segment is selected and used as the reference signal to re-process the current time-series signal segment. After processing of each time-series signal segment completes, the sliding window is shifted to define a next segment of the time-series signal with a least a partial overlap occurring with the previously processed signal segment. The present method repeats for each time-series signal segment on a continuous basis or until a termination criteria has been met. In such a manner, the subject's cardiac pulse rate is estimated on a continuous monitoring basis in a computationally efficient manner.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
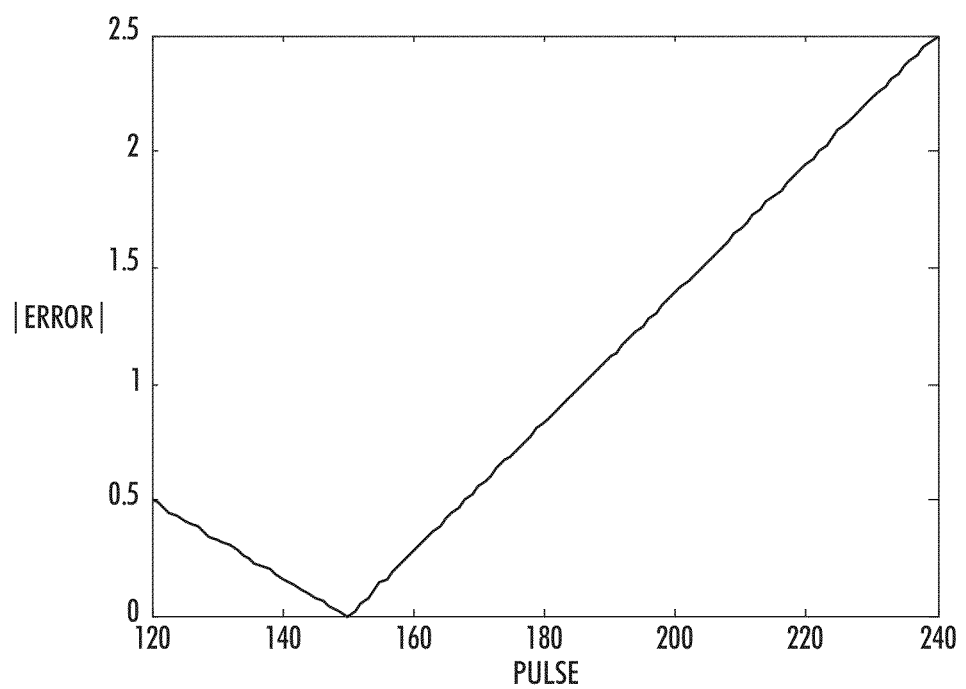
FIG. 1 is an error plot with one infant video between an input heart rate to an extracted heart rate using the previously disclosed method for a limited range of 120 to 240 bpm.

What is disclosed is a computationally efficient system and method for estimating a subject's cardiac pulse rate from multi-channel source video data that can be used in a continuous monitoring mode with a high degree of measurement accuracy.

Non-Limiting Definitions

A "subject of interest", as used herein, refers to a human having a cardiac function. One example subject of interest is shown and discussed with respect to patient 205 of FIG. 2. Although the term "human", "person", or "patient" may be used throughout this text, it should be appreciated that the subject of interest may be something other than a human being such as, for instance, an animal. Use of "person" or "patient" is not to be viewed as limiting the appended claims strictly to humans.

A "video" is a time-varying sequence of images captured using a video camera capable of acquiring video data over multiple data acquisition channels. The video may also contain other components such as, audio, time reference signals, noise, and the like.

A "time-series signal" refers to a time varying signal generated from images of the captured video. The time-series signal generated from the captured video images can be RGB signals, IR signals, a combination of RGB and IR signals, multi-spectral signals, or hyperspectral signals. Time-series signals may be generated in real-time from a streaming video as in the case of continuous patient monitoring.

"Receiving a time-series signal" is intended to be widely construed and means to retrieve, receive, capture with a video capture device, or otherwise obtain a time-series signal for processing in accordance with the teachings hereof. In various embodiments, the time-series signal is retrieved from a remote device such as a computer workstation over a wired or wireless network or obtained on a continuous basis from a video stream.

A "sliding window" refers to a window of size win_size which identifies successive segments of a time-series signal for processing in accordance with the teachings hereof. The window has a size which can be different for one or more time-series signal segments. The window size can also be based on a performance characteristic of the blind source separation method used for constrained source separation.

A "seed reference signal" is a reference signal used by a constrained independent component analysis (cICA) algorithm to perform constrained source separation on a particular time-series signal segment. On each iteration of running constrained source separation, an estimated output signal is generated. If, as determined by a measure of closeness, the estimated output signal produced on the current iteration is not within a threshold level then the seed reference signal is updated to obtain an updated reference signal used by the cICA algorithm as a seed reference signal on a next iteration. In a manner as more fully described herein, the updated reference signal is used on a next iteration of constrained source separation performed on the current time-series signal segment to obtain another estimated source signal. On each iteration, a closeness measure is determined and, in response to the measure of closeness not being within a pre-defined threshold, the reference signal is again updated and constrained source separation is performed yet again. The process repeats until the estimated source signal is within a threshold limit or a pre-determined number of iterations have occurred. It should be appreciated that, on the first iteration, the seed reference signal is used for cICA processing of the current time-series signal segment, with the seed reference signal being updated on each successive iteration of cICA processing until a termination criteria is reached.

"Updating the reference signal" means changing at least one aspect of the reference signal. The reference signal may be updated by, for example, changing a frequency of the signal, or by changing an amplitude or phase of the signal.

The reference signal may be updated by altering a waveform of the signal. The waveform can be, for example, a sine wave, a square wave, a user defined shape such as that obtained from an ECG signal, or a cardiac pulse waveform derived from apriori knowledge of the subject's cardiac history.

"Conditioning the signal" means processing the estimated source signal to remove artifacts. Artifacts include undesirable periodic signals, background noise and other unwanted environmental factors. As disclosed herein, the conditioned estimated source signal becomes the seed reference signal used for to perform constrained source separation on a time-series signal segment defined by the sliding window.

"Cardiac function" refers to the function of the heart and, to a large extent, to the cardio-vascular system. In most species, the heart comprises muscle which repeatedly contracts to pump blood throughout the vascular network. Cardiac function can be impacted by a variety factors including age, stress, disease, overall health, and the like. Cardiac function can also be affected by environmental conditions such as altitude and pressure.

A "cardiac pulse" is a pressure wave that is generated by the subject's heart (in systole) as the heart pushes a volume of blood into the arterial pathway. Arterial movement, as a result of this pressure wave, can be sensed by tactile and electronic methods. A frequency of the cardiac pulse is the pulse rate measured over time, typically recorded in beats per minute (bpm). A resting adult human has a cardiac pulse rate of about 72 bpm. The frequency range of the human cardiac pulse is between about 50 bpm to 240 bpm. Each species have their own "normal" heart rate and thus their own cardiac pulse frequency range. Heart rate is proportional to the cardiac output, i.e., the volume of blood the heart can pump expressed in L/min (~5 L/min in an adult human). Cardio Output is often defined as: CO=SV·HR, where SV is stroke volume and HR is heart rate (in bpm). Stroke volume can be affected by valvular dysfunction and ventricular geometric form.

"Blind Source Separation" is a technique for the recovery of unobserved signals from a mixed set of observed signals without any prior information being known about how the signals were mixed. Typically, the observed signals are acquired as output from sensors where each sensor receives or otherwise detects a different proportion of mixture of source signals. Blind source separation is a method for separating the source signals. One form of blind source separation is independent component analysis.

"Independent Component Analysis" (ICA) is a decomposition technique used for uncovering independent source signal components from a set of observations that are composed of linear mixtures of underlying sources, i.e., independent components of the observed data. These independent components (ICs), also called sources or factors, can be found by ICA methods. ICA is superficially related to principal component analysis. ICA is a powerful technique which is often capable of identifying underlying sources when classic methods have failed. Data analyzed by ICA can originate from many different kinds of applications including source signals comprising time-series signals. In practice, the ordering of the ICs is quite important to separate non-stationary signals or signals of interest with significant statistical characteristics. Constraints can be placed on this technique.

"Constrained source separation" is a constrained independent component analysis method for separating time-series signals into additive sub-components using a seed reference signal as a constraint. Not all constraints can be used for constrained independent component analysis (cICA) because some constraints infringe classical ICA equivariant properties. Constraints that define or restrict the properties of the independent components should not infringe the independence criteria. Additional conditions can be incorporated using, for example, sparse decomposition of signals or fourth-order cumulants into the contrast function, to help locate the global optimum separating the components.

cICA is essentially a constraint minimization problem, i.e., minimize function $C(y)$ subject to constraints: $g(y:W) \leq 0$ and/or $h(y:W)=0$, where $C(y)$ is a contrast function, and where constraints:

$$g(y:W) = [g_1(y:W), g_2(y:W), \ldots, g_v(y:W)]^T$$

and $$h(y:W) = [h_1(y:W), h_2(y:W), \ldots, h_v(y:W)]^T$$

define vectors of u (inequality) and v (equality), respectively. Statistical properties (e.g., consistency, asymptotic variance, robustness) of cICA depend on the choice of the contrast function $C(y)$ and the constraints in the objective function.

More formally, let the time-varying observed signal be: $x=(x_1, x_2, \ldots, x_n)^T$, where x is a linear mixture of ICs $c_i$ of signal $c=(c_1, c_2, \ldots, c_m)^T$. Therefore, x=Ac where matrix A (of size n×m) represents the linearly mixed channels observing x. Demixing matrix W recovers components $c_1, c_2, \ldots, c_m$ of signal x which, in turn, produces signal y=Wx, given by: $y=(y_1, y_2, \ldots, y_m)^T$, with minimal knowledge of A and c. Reference signal $r=(r_1, r_2, \ldots, r_l)^T$ carries traces of information of desired signal c and need not be exact to the original sources. A measure of closeness is estimated between signal $y_i$ and reference signal $r_i$ by the norm $\epsilon(y_i, r_i)$. The components of output signal y are mutually independent and correspond to l original sources mixed in observed signal x. The matrix A is an m×m square matrix when there are m number of observed signals and m number of sources. Demixing matrix W is l×m (l<m). The minimum norm $\epsilon(y_i, r_i)$ of all outputs y indicates that signal $y_i$ is closest to reference signal $r_i$. If this component is closest to the reference signal then $\epsilon(y_i^*, r_i) < \epsilon(y_i^o, r_i)$, where $y_i = y_i^*$ is the output signal producing the desired IC closest to $r_i$, and $y_i^o$ is the next closest output signal. cICA recovers the closest IC if the closeness measure and threshold are properly selected. Success depends on the selection of threshold parameter $\xi_i$: $\epsilon(y_i^*, r_i) - \xi_i \leq 0$. None of the other m−1 sources will correspond to reference signal $r_i$ if $\xi_i$ is in the scalar range of $[\epsilon(y_i^*, r_i), \epsilon(y_i^o, r_i)]$.

The interested reader is respectfully directed to the following incorporated texts: "*Independent Component Analysis*", ISBN-13: 978-0471405405, "*Independent Component Analysis: Principles and Practice*", ISBN-13: 978-0521792981, and "*Approach and Applications of Constrained ICA*", Wei Lu and Jagath C. Rajapakse, IEEE Transactions On Neural Networks, Vol. 16, No. 1, pp. 203-212, (January 2005).

Example Image Capturing System

Figure 2:
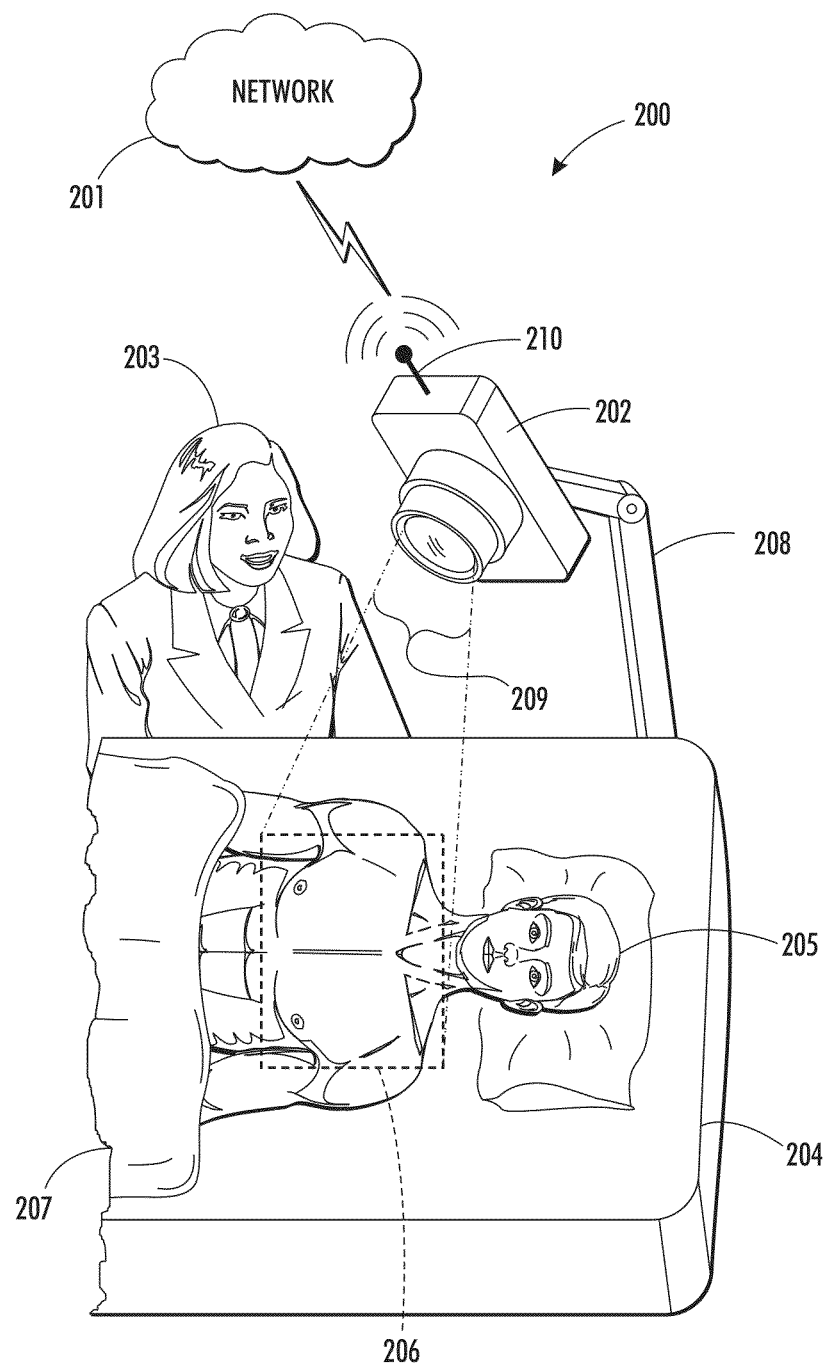
FIG. 2 illustrates an example system for capturing a multi-channel signal of a subject of interest.

Reference is now being made to FIG. 2 which illustrates an example imaging system for capturing a multi-channel signal of a subject of interest.

Examination room 200 has an example image capturing system 202 being operated by technician 203 standing at the bedside 204 of subject of interest 205 shown resting his head on a pillow while most of his body is partially covered by sheet 207. Camera system 202 is rotatably fixed to support arm 208 such that the camera's field of view 209 can be directed by nurse 203 onto an area of exposed skin of a chest area 206 of patient 205 for continuous monitoring of cardiac function. Support arm 208 is on a set of wheels so that the image capture system can be moved from bed to bed and room to room. Although patient 205 is shown in a prone position lying in a bed, it should be appreciated that images of the subject of interest being monitored for cardiac function can be captured while the subject is positioned in other supporting devices such as, for example, a chair or wheelchair, standing up, including walking or moving. The embodiment of FIG. 2 is not intended to be viewed as limiting the scope of the appended claims in any respect. Camera system 202 captures video images of the subject of interest to be monitored for cardiac function. The captured video images comprises multi-channel source data such as RGB and/or multi-spectral acquired over time. Camera 202 comprises imaging sensors which may be a single sensor or a sensor array including a plurality of individual or separate sensor units. A central processor integral to camera 202 and in communication with a memory (not shown) and the imaging sensor may take a variety of forms each having the capability of detecting changes in the status of sensors and outputting an alarm, notice, report, and the like if a change in any hardware or software of the camera has been detected. Other sensors contemplated are capable of sensing a change of position or status of patient 205 and issue an alarm or notification via transmission element 210 to a nurse, doctor, or technician in the event that the cardiac function of the patient falls outside a set of pre-defined parameters. Antenna 210 is used to communicate the captured images to various remote devices. Transmitter 210 may be a wired (e.g., Ethernet) connection utilizing an Ethernet network consisting of Ethernet cables and an Ethernet hub that is in communication with a network 201. Camera system 202 may include both wireless and wired elements and may be connected via other means such as coaxial cable, radio frequency, Bluetooth, or any other manner for communicating data. Network 201 receives the transmitted video signals and wirelessly communicates the received signal data to devices such as, for instance, a workstation with a graphical display device, or a handheld device such as an iPhone, iPad, notebook, and the like. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Techniques for placing devices in networked communication are well established. Therefore, a further discussion as to specific techniques for networking devices has been omitted. Any of the networked devices may include a network interface card or system.

Example Block Diagram

Figure 3:
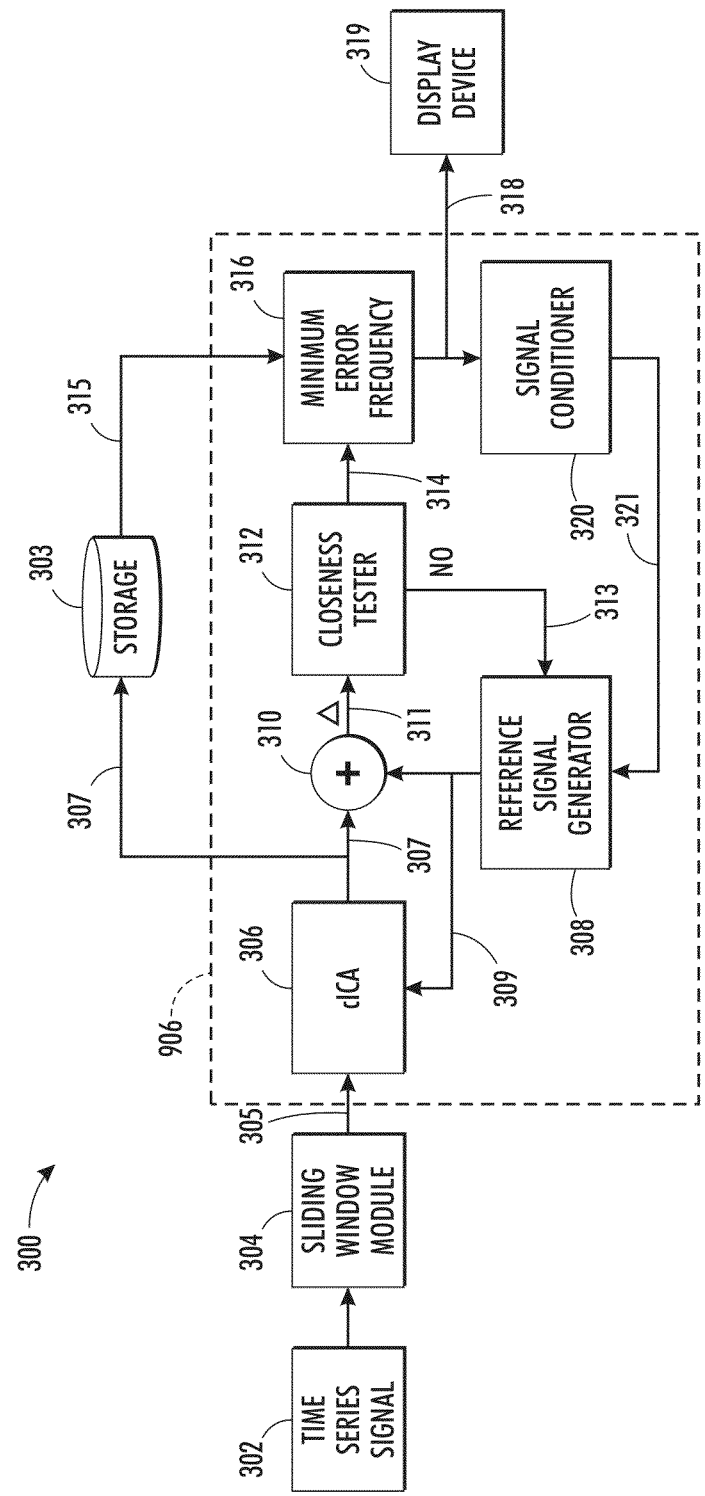
FIG. 3 is a block diagram of one embodiment of a signal processing system for performing various aspects of the present system and method for continuous cardiac pulse rate estimation.

Reference is now being made to FIG. 3 which is a block diagram of one embodiment of a signal processing system for performing various aspects of the present system and method for continuous cardiac pulse rate estimation.

Received time-series signal 300 is provided to sliding window module 304 which defines a sliding window of size win_size and, on each iteration, uses that sliding window to identify overlapping segments of the time-series signal for processing. The received time-series signal is generated from video images captured of a subject of interest being monitored for cardiac function in accordance herewith. On a first iteration, sliding window module 304 defines a first time-series segment 305 for processing. With each successive iteration, sliding window module 304 identifies a successive time-series signal segment 305 for processing. Between successive iterations, the overlap in data frames is significant enough to ensure consistency in signal recovery estimation. Reference signal generator 308 generates, on a first iteration, a seed reference signal 309 which has a frequency range that approximates a frequency range of the subject's cardiac pulse. Signal conditioner 320 conditions signal 316 to obtain a next reference signal for use in the next iteration. On each iteration, updated reference signal 309 is provided to cICA algorithm 306 which produces a next estimated source signal 307. Each of the produced estimated source signals 307 are provided to storage device 303. On each iteration, reference signal 309 is provided to comparator 310 wherein it is compared against the produced estimated source signal 307 such that a difference 311 therebetween can be determined. Closeness test module 312 determines whether the difference 311 between reference signal 309 and estimated source signal 307 are within a pre-defined threshold (or if a pre-determined number of iterations have occurred). If it is determined that closeness has not occurred then signal 313 is sent to reference signal generator 308 to update reference signal 309 by changing the reference signal frequency, amplitude, phase, and/or waveform. The updated reference signal is then again provided to cICA 306 which, on this iteration, produces a next estimated source signal 307. The next estimated source signal 307 produced by cICA 306 is again compared to seed reference signal 309 and a difference 311 therebetween determined. New difference 311 is provided to closeness tester 312 which again determines whether closeness has occurred to within a pre-defined threshold level (or if a pre-determined number of iterations have occurred). If closeness has not occurred then the process repeats. One of ordinary skill will recognize the iterative nature of the signal processing system of FIG. 3. Upon closeness (which terminates the current cycle of iterations), signal 314 is provided to minimum error frequency determinator 316 which retrieves the estimated source signals (collectively at 315) produced for the current time-series segment by cICA 306 and identifies which of the estimated source signals (307) had a minimum error, i.e., was closest to the seed reference signal used by the cICA 306. The frequency of the estimated source signal which achieved a minimum error is determined to be the estimated cardiac pulse rate 318 for the current time-series signal segment 305. In this embodiment, estimated cardiac pulse rate 318 is provided to display device 319. In other embodiments, the estimated cardiac pulse rate is provided to a processor to determine whether the pulse rate is within acceptable parameters set for the subject, and an alert signal is transmitted to a monitoring device in the event that the estimated cardiac pulse rate, for any given segment, is outside an acceptable limit or range. For the next time series segment 305, the closest estimated output signal, as determined by the previous iteration, is provided to signal conditioner 320 wherein this signal is conditioned by removing artifacts. One method for conditioning a time-series signal may involve constructing a square wave or a sine wave or a user defined shape such as that obtained from an ECG signal or a PPG signal and is disclosed in the above-incorporated U.S. Patent Application entitled: "Estimating Cardiac Pulse Recovery From Multi-Channel Source Data Via Constrained Source Separation", U.S. patent application Ser. No. 13/247,683, by Mestha et al. The conditioned signal is provided to reference signal generator 308 and is used as seed reference signal to initiate processing of the next time-series segment until closeness is determined (or a pre-determined number of iterations have occurred). The frequency of the closest estimated source signal is determined to be the subject's estimated cardiac pulse rate, for this particular time-series signal segment. The process repeats for each time-series signal segment defined by the sliding window until all signal segments have been processed or until a termination criteria is met.

Although the block diagram of FIG. 3 shows an embodiment wherein current result 318 is conditioned and used as a seed reference signal for the next successive time-series segment, it should also be appreciated that any of the resulting signals 318 obtained as a result of having processed any of the previous segments 305 can be used as a seed reference signal to initiate processing of the current time-series signal segment.

Flow Diagram of One Embodiment

Figure 4:
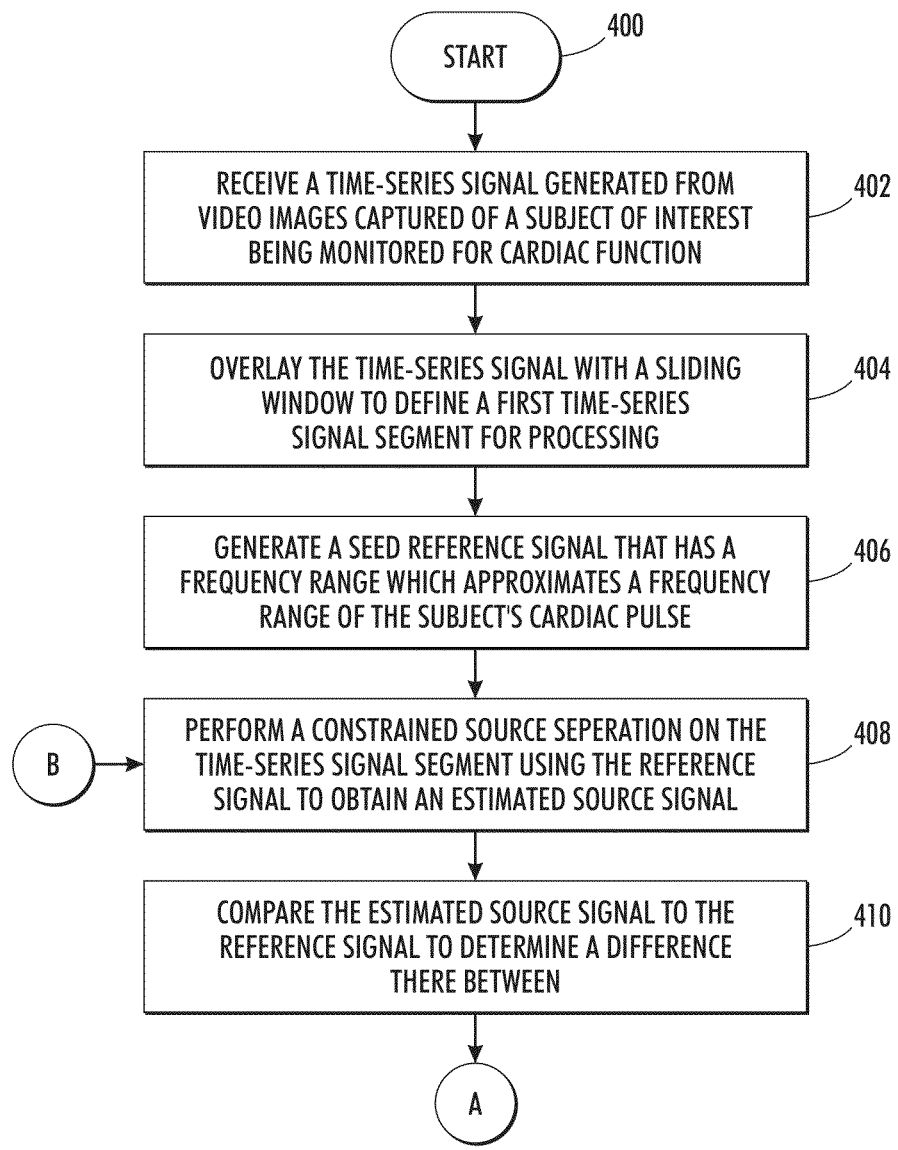
FIG. 4 is a flow diagram which illustrates one embodiment of the present method for continuous cardiac pulse rate estimation from multi-channel source video data captured of the subject of FIG. 2 being monitored for cardiac function.

Reference is now being made to the flow diagram of FIG. 4 which illustrates one embodiment of the present method for continuous cardiac pulse rate estimation. Flow processing starts at step 400 and immediately proceeds to step 402.

At step 402, receive a time-series signal generated from video images captured of a subject of interest intended to be monitored for cardiac function. The received time-series signal can be RGB signals, IR signals, RGB and IR signals, multi-spectral signals, or hyperspectral signals.

At step 404, overlay the time-series signal with a sliding window of size win_size to define a first time-series signal segment for processing.

At step 406, generate a seed reference signal which has a frequency range which approximates a frequency range of the subject's cardiac pulse. The reference signal can be received from a remote device over a network or retrieved from a memory, storage device, or obtained from a database of reference signals.

At step 408, perform constrained source separation on the time-series signal segment using a reference signal. Each iteration of the constrained source separation method produces an estimated source signal.

At step 410, compare the estimated source signal to the reference signal (used in step 408) to determine an amount of a difference therebetween. This difference is the error between the estimated source signal produced as a result of having performed step 408, and the reference signal.

Figure 5:
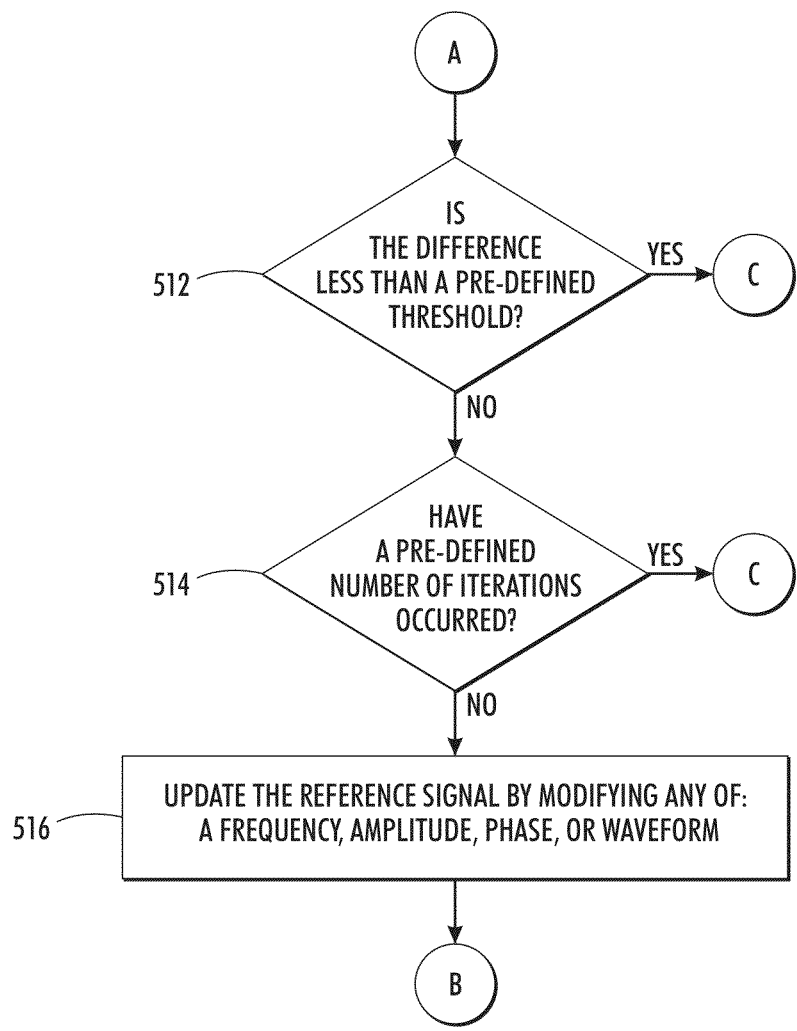
FIG. 5 is a continuation of the flow diagram of FIG. 4 with flow processing continuing with respect to node A.

Reference is now being made to the flow diagram of FIG. 5 which is a continuation of the flow diagram of FIG. 4 with flow processing continuing with respect to node A.

At step 512, a determination is made whether the difference (of step 410) is within a pre-determined threshold value. If not then processing continues with respect to step 514 wherein a determination is made whether a pre-defined number of iterations have occurred. If not then processing continues with respect to step 516 wherein the reference signal is updated. As discussed, the reference signal may be updated by changing any a frequency, an amplitude, a phase, shape and a waveform of the reference signal. Changing the waveform may comprise changing any of: a sine wave, a square wave, a user-defined shape obtained from an ECG signal, and/or a cardiac pulse waveform derived from the subject. Upon having updated the reference signal in step 516, processing repeats with respect to node B wherein, at step 408, constrained source separation is again performed on the current time-series signal segment using the updated reference signal. Constrained source separation produces a next estimated source signal which, at step 410, is compared to the updated reference signal to determine an amount of an error therebetween. If, at step 512, the difference is not less than a pre-defined threshold and, at step 412, a pre-determined number of iterations have not yet occurred then, at step 516, the reference signal is again updated. Processing repeats in such a manner until the occurrence of either the difference (of step 512) is less than the pre-defined threshold or a pre-determined number of iterations have occurred (of step 514). If, at step 512, the difference produced as a result of the comparison of step 410 is less than the pre-defined threshold then processing continues with respect to node C. If, at step 514, the pre-defined number of iterations has occurred then processing continues also with respect to node C.

Figure 6:
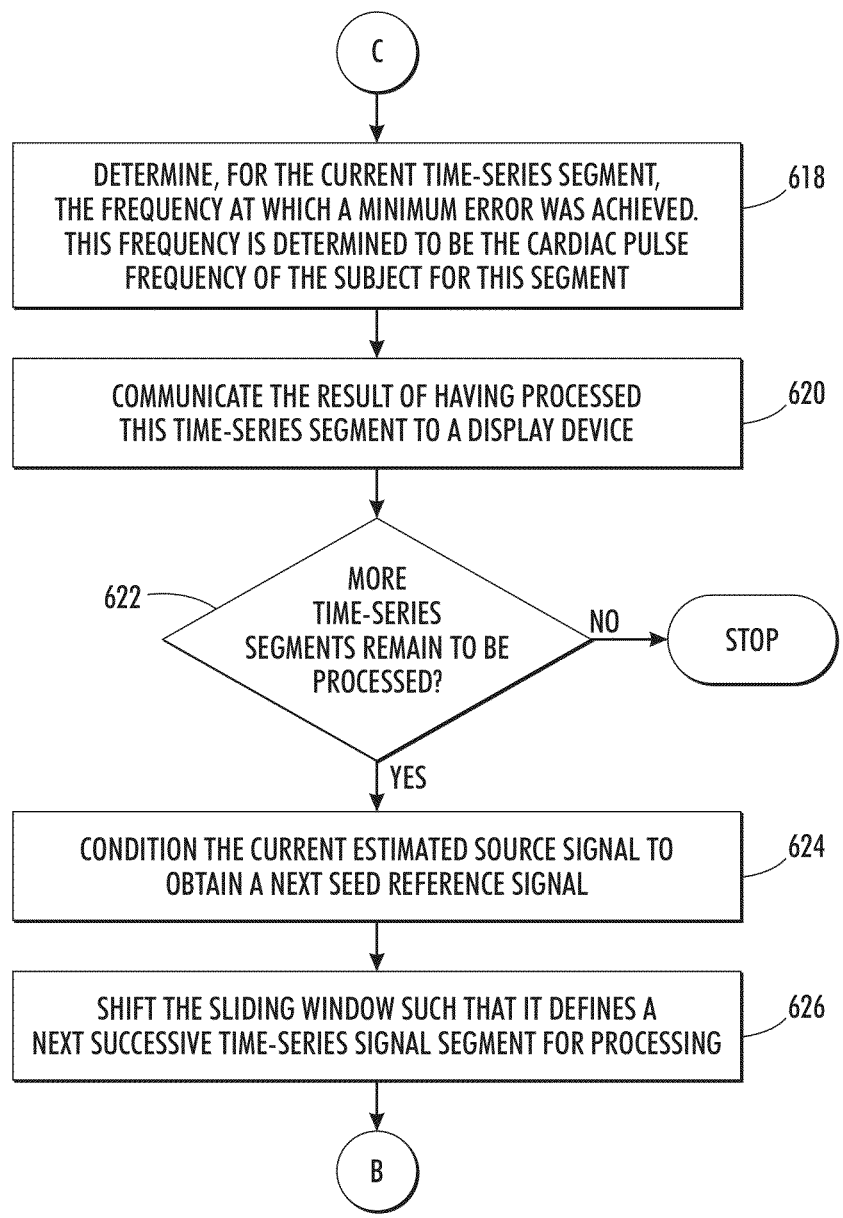
FIG. 6 is a continuation of the flow diagram of FIG. 5 with flow processing continuing with respect to node C.

Reference is now being made to the flow diagram of FIG. 6 which is a continuation of the flow diagram of FIG. 5 with flow processing continuing with respect to node C.

At step 618, the frequency at which a minimum error was achieved (between the estimated source signal and the reference signal of step 410) is determined for the current time-series signal segment being processed. This frequency is determined to be the subject's estimated cardiac pulse rate for the current time-series segment (of step 404).

At step 620, the result (of step 618) is communicated to a display device. The results may be further processed for a determination as to whether the subject's estimated cardiac pulse rate is within acceptable limits. If not then a signal can be generated to notify, for example, the patient's cardiac physician or a nurse.

At step 622, a determination is made whether more time-series signal segments remain to be processed. If not then, in this embodiment, further processing stops. Otherwise, processing continues with respect to step 624.

At step 624, condition the estimated source signal with the minimum error (of step 618) to produce a next reference signal to be used by the constrained source separation algorithm to processed the next time-series signal segment.

At step 626, shift the sliding window such that it defines a next successive time-series signal for processing. Each successive shifting of the sliding window at least partially overlapping the previous time-series signal segment. The overlap in data frames is preferably significant enough to ensure consistency in signal recovery estimation. This will depend, to a large extent, on the time-series signals being processed and may be determined by trial and error or based upon past experience in processing such signals. Once a next time-series signal segment has been identified, processing repeats with respect to node B wherein constrained source separation is performed on this signal segment using the next reference signal (of step 624). Processing continues in such a manner until, at step 622, it is determined that no more time-series signal segments remain to be processed, and further processing stops.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Sliding Window Defining Overlapping Signal Segments

Figure 7:
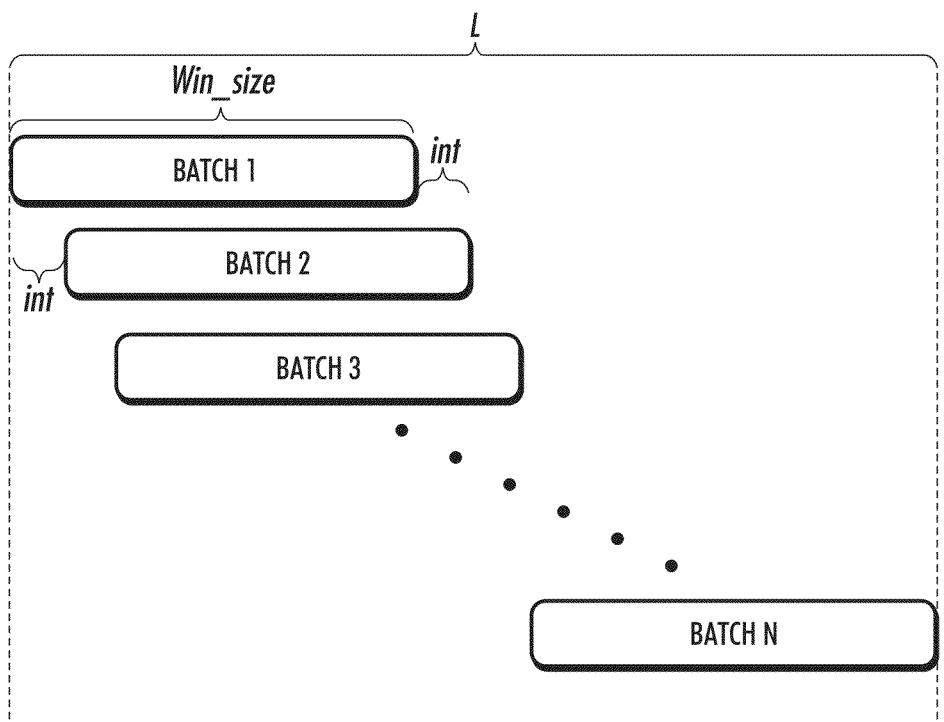
FIG. 7 illustrates a sliding window which is repeatedly shifted to define overlapping successive time-series signal segments for processing in accordance with various embodiments hereof.

Reference is now being made to FIG. 7 which illustrates a sliding window which is repeatedly shifted to define overlapping successive time-series signal segments for processing in accordance with various embodiments hereof.

Video frames are spatially averaged over all pixels per frame to obtain RGB time varying signals or raw traces. Batches are created by sliding a window of length 30 seconds with 96.67% overlap between consecutive batches which means using only 1 second of new frames and retaining 29 seconds of frames from previous batch. However, the window length and the overlap length are resizable depending on rate of change of patient's pulse rate.

Functional Block Diagram for Continuous Cardiac Pulse Rate Monitoring

Figure 8:
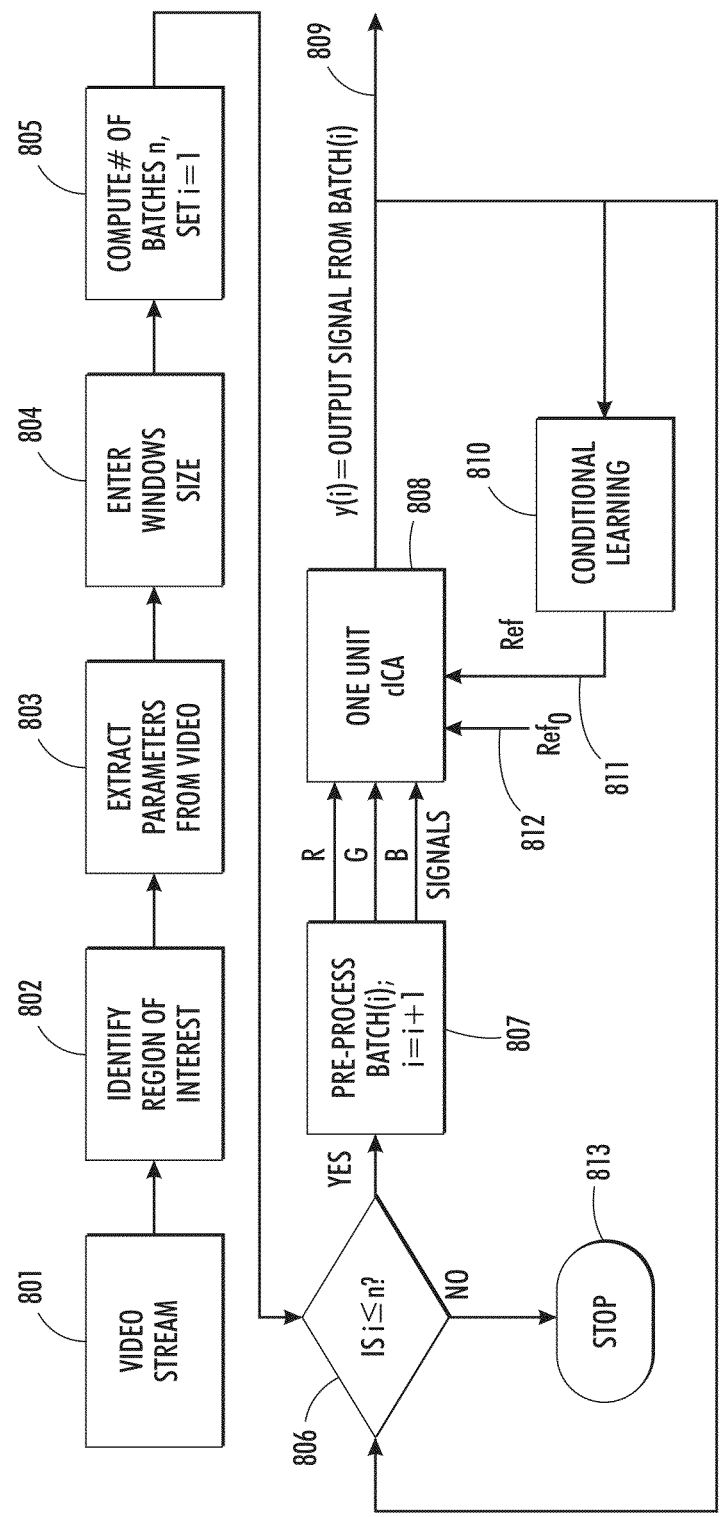
FIG. 8 shows an example block diagram of one embodiment of the present method for continuous pulse rate monitoring with computational blocks for a video stream comprised of n number of batches, the functional steps being repeated as new video streams arrive.

Reference is now being made to FIG. 8 which illustrates an example functional block diagram 800 of an embodiment for continuous pulse rate monitoring with computational blocks for a video stream comprised of n number of batches, the functional steps being repeated as new video streams arrive.

In block 801, the video stream is captured and provided to video pre-processing block 802 wherein regions of interest of the subject being monitored are identified or otherwise selected. In block 803, parameters are extracted from the video such as video length, frame speed, and the like. In block 804, the user enters various parameters such as window size, threshold level, max number of iterations, and the like. In block 805, the number of batches n is computed based upon the length of the time-series signal and the size of the user-defined window. Batch counter i is initialized to 1. On the first iteration, a determination is made (in decision block 806) whether batches remain to be processed. If so then, in block 807, the current batch is pre-processed which includes continuous time band pass filtering (with an adjustable bandwidth depending on patient's pulse rate), whitening and normalizing. The pre-processed R,G,B signals associated with the time-series signal segment defined by the current window. The batch counter is incremented. In block 808, constrained source separation is performed on the time-series signal segment using, on a first iteration, the seed reference signal 812. A result of having performed constrained source separation is output signal y(i) corresponding to batch(i). Constrained source separation is performed on processed signals with the PPG signal measured from a Biopac system (or a square wave generated by incorporating prior knowledge about the patient's pulse rate) is used as reference $Ref_0$ to batch #1. cICA is based on constrained optimization using Newton-like learning to separate underlying source which is not identical but close to the reference signal (to within a measure of closeness). The output signal 809 resembles a PPG signal and pulse rate, and is computed by taking the Fast Fourier Transform (FFT) of this signal. On successive iterations, each output signal 809 corresponding to the previous batch is used by Conditional Learning Block 810 to learn the next reference signal 811 for the next batch such that pulse signals can be extracted for the next successive batch. If the pulse rate generated from the current batch exceeds the pulse rate generated from the previous batch (as measured by a pre-defined threshold value such as, for example, 13 bpm) the current estimated pulse rate is rejected and the previous pulse rate is retained in order to avoid an undesired jump in pulse rate caused by certain artifacts. This loop continues until all batches are processed and a continuous pulse rate achieved for the subject over time.

Example Functional Block Diagram

Figure 9:
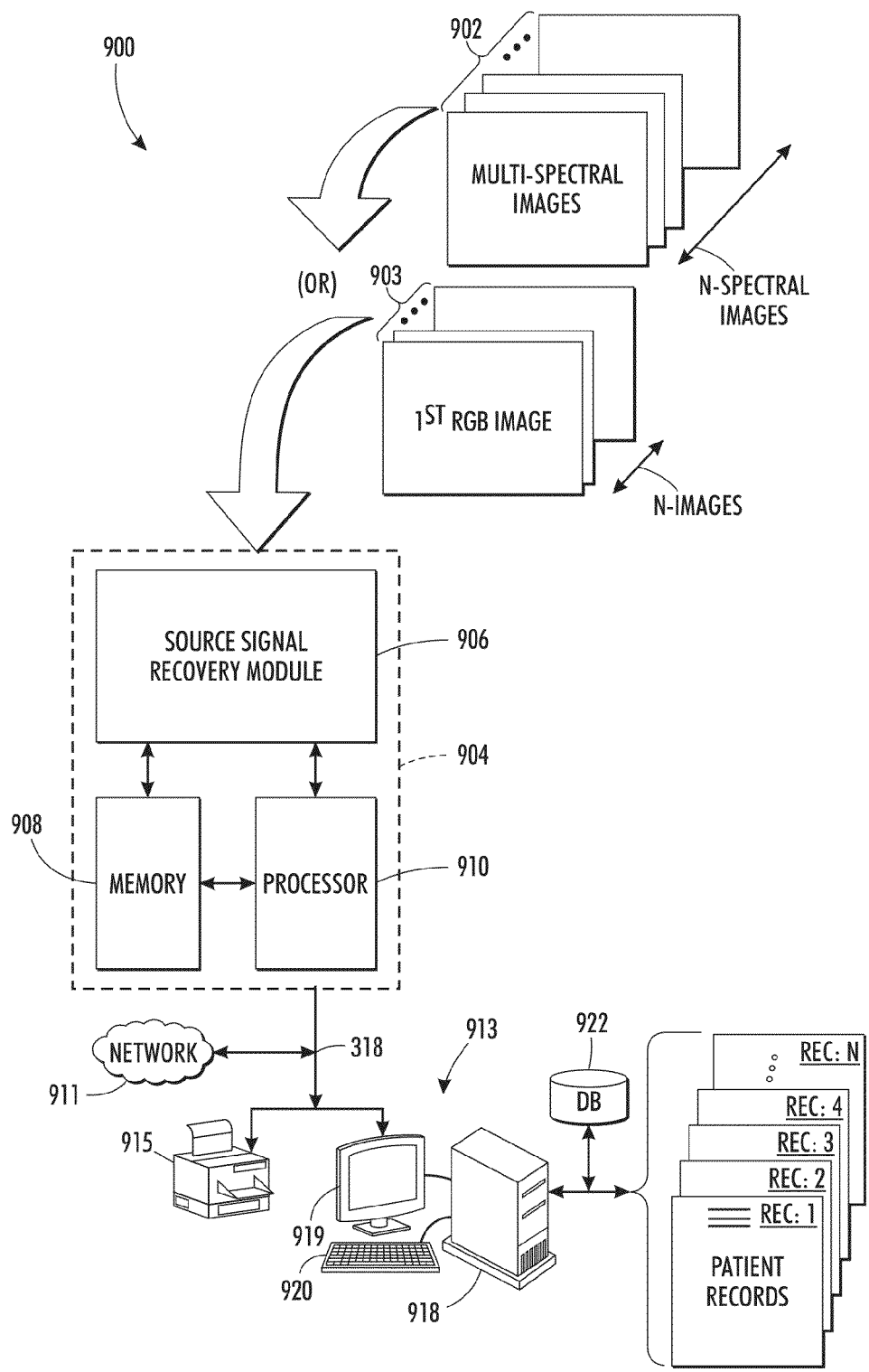
FIG. 9 illustrates a block diagram of one example signal processing system for performing various aspects of the present method as shown and described with respect to the flow diagrams of FIGS. 4-6.

Reference is now being made to FIG. 9 which illustrates a block diagram of one example processing system 900 for implementing various aspects of the present method described with respect to the flow diagrams of FIGS. 4-6.

The embodiment of FIG. 9 receives a sequence of video images captured of a subject of interest intended to be monitored for cardiac function. The captured video images are either a plurality of multi-spectral images 902 captured using a multi-spectral camera or a plurality of RBG images 903. The sequence of images 902 or 903 collectively comprises multi-channel source data acquired over time. Signal processing system 904 receives the multi-channel source data into source signal recovery module 906 which performs all the functionality as described in embodiment of FIG. 3. Memory 908 and CPU 910 facilitate the processing and output an estimated cardiac pulse rate 318. Estimated cardiac pulse rate 318 is communicated to workstation 913 and multi-function print system device 915 for further processing or for rendering. The estimated cardiac pulse rate may further be communicated to remote devices over network 911. Many aspects of network 911 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Computer workstation 913 is shown comprising a computer case 918 housing a motherboard, CPU, memory, interface, storage device, and a communications link such as a network card. The computer workstation is also shown having a display device 919 such as a CRT, LCD, or touchscreen display. An alphanumeric keyboard 920 and a mouse (not shown) effectuate a user input. In the embodiment of FIG. 9, computer system 913 implements database 922 wherein various records are stored, manipulated, and retrieved in response to a query. Although the database is shown as an external device, the database may be internal to computer case 918 mounted on a hard disk housed therein. A record refers to any data structure capable of containing information which can be indexed, stored, searched, and retrieved in response to a query. Patient information can be stored and/or retrieved to any of the records in database 922. It should be appreciated that the workstation has an operating system and other specialized software configured to display a variety of numeric values, text, scroll bars, pull-down menus with user selectable options, and the like, for entering, selecting, or modifying information displayed on the display device.

Any of the modules and processing units of FIG. 9 are in communication with workstation 913 via pathways (not shown) and may further be in communication with one or more remote devices over network 911. It should be appreciated that some or all of the functionality for any of the modules of system 904 may be performed, in whole or in part, by components internal to workstation 913 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through network 911.

Performance Results

Figure 10:
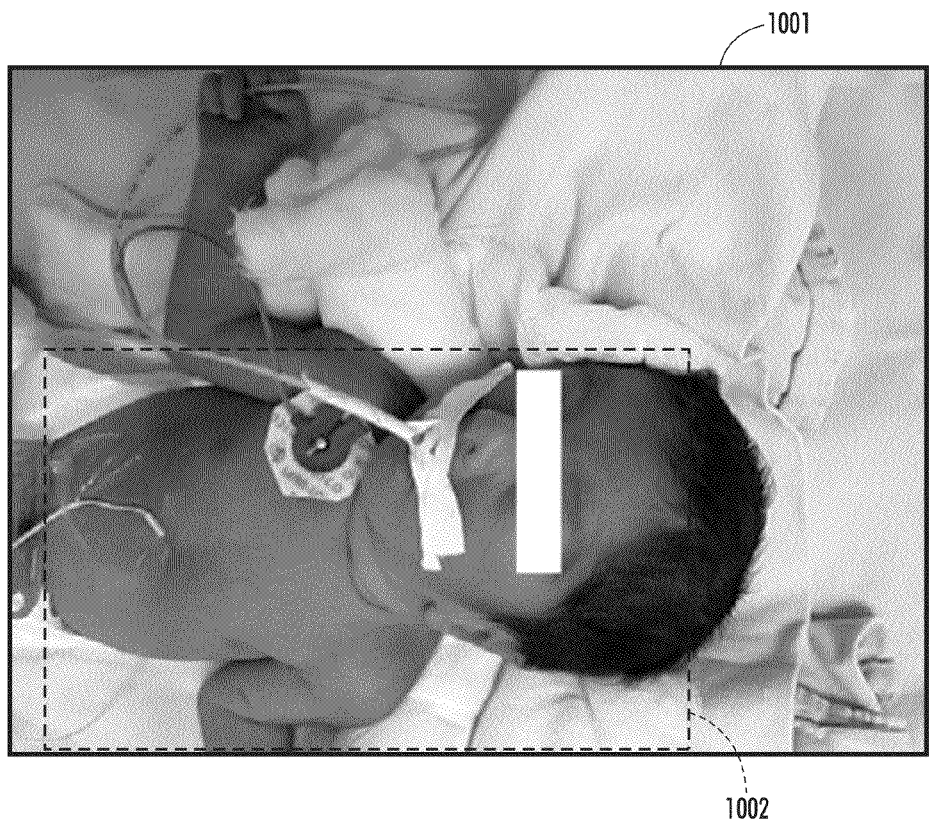
FIG. 10 shows an image of an infant in a neonatal intensive care unit (NICU) with a region of interest of exposed skin being identified using custom software.
Figure 11:
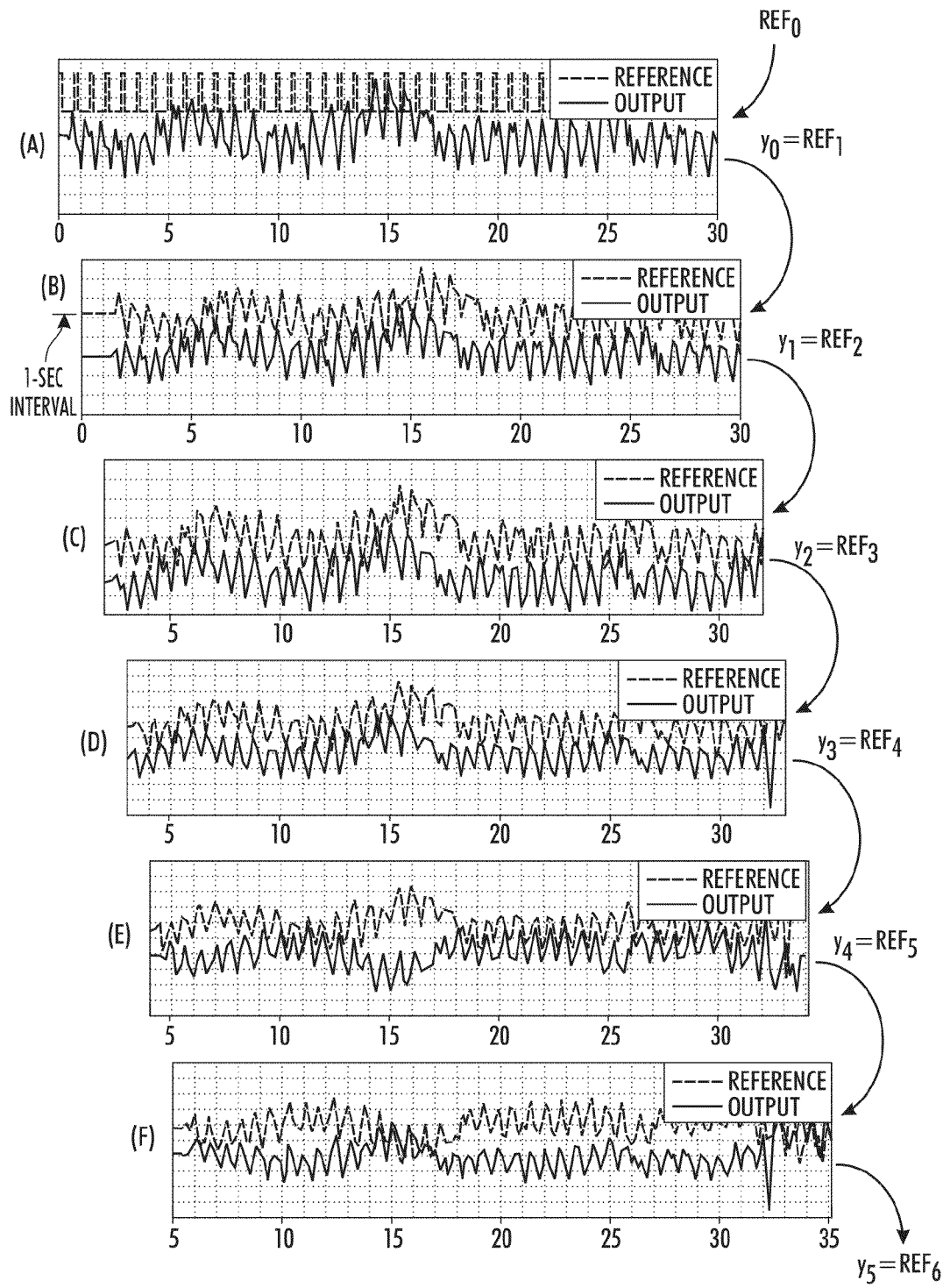
FIG. 11 shows pulse signals extracted from a video of the infant of FIG. 10 via successive overlapping batch processing in accordance with the present method.

In order to illustrate the effect of continuous pulse monitoring, video recordings were produced using a standard RGB digital camera at 30 frames per second (fps) with pixel resolution of 1280×720 and saved in AVI format. Each video was of length two minutes and was captured on infants in a neonatal ICU environment. A custom algorithm was used to detect a region of interest (ROI) comprising human skin in video frames, FIG. 10 shows an image 1001 of an infant in a neonatal intensive care unit (NICU) with a region of interest 1002 of exposed skin being identified in the video stream using custom software. The frames of the video were reduced to raw traces (RGB channels) with respect to time by spatially averaging all pixels in the ROI in each frame. The RGB traces were pre-processed, which included bandpass filtering to the expected pulse rate range of the infant, whitening followed by normalizing to yield traces of zero-mean unit-variance signal. The processed traces were fed to the one-unit cICA (808 of FIG. 8) with the conditioned PPG signal obtained from a Biopac system from the same infant. The frames were batch processed using a 30 second sliding window with 1 second increments. For each batch, the output from a previous batch was incorporated as prior knowledge to the cICA. FIG. 11 shows pulse signals extracted from a video of the infant of FIG. 10 via successive overlapped batch processing in accordance with the present method. Pulse computation for the first batch is shown in FIG. 11 at plot (A) where the seed reference signal $Ref_0$ is used to perform constrained source separation on the first time-series signal segment defined by the window of size win_size=30 to obtain estimated output signal $(y_0)$ on the first iteration. The obtained estimated output signal $y_0$ serves as reference $Ref_1$ for the one-unit cICA to obtain next estimated source signal $y_1$ and so on in a sequential manner for successive batches (B) through (F), until all the time-series signal segments have been processed accordingly.

Figure 12:
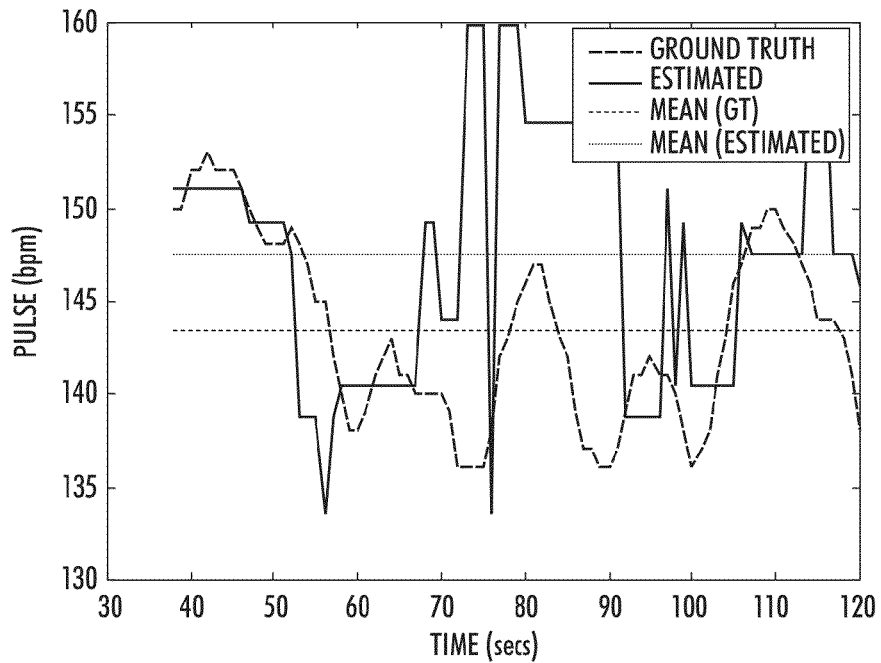
FIG. 12 shows estimated and true pulse rate plotted against time using a prior art method.
Figure 13:
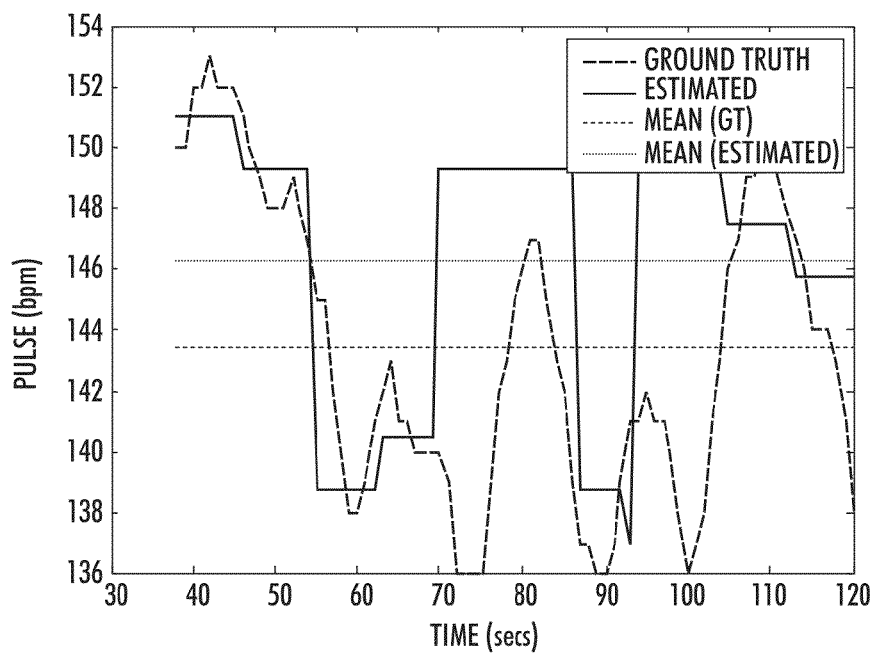
FIG. 13 shows estimated and true pulse rate plotted against time using the present method.
Figure 14:
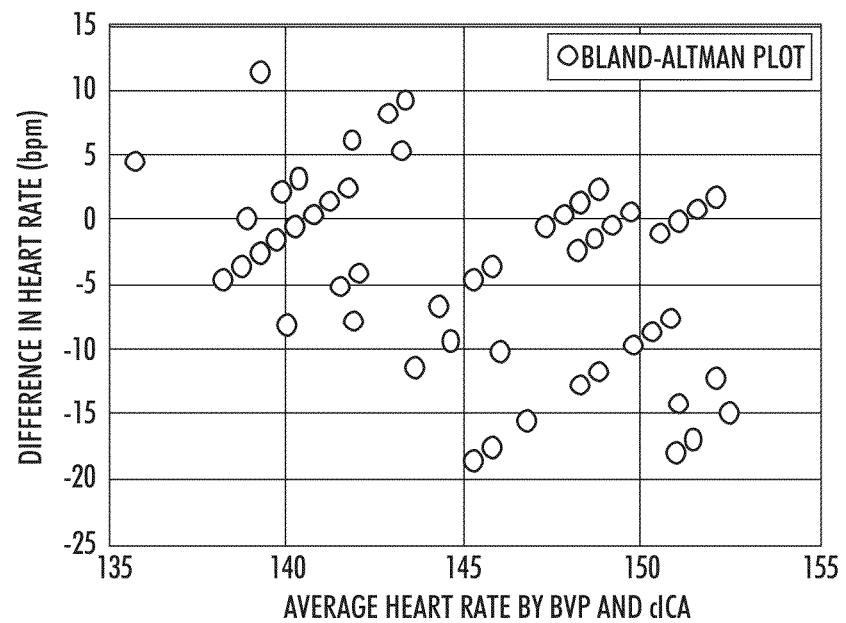
FIG. 14 shows Bland-Altman plots between estimated and true pulse using a prior art method (FIG. 12)
Figure 15:
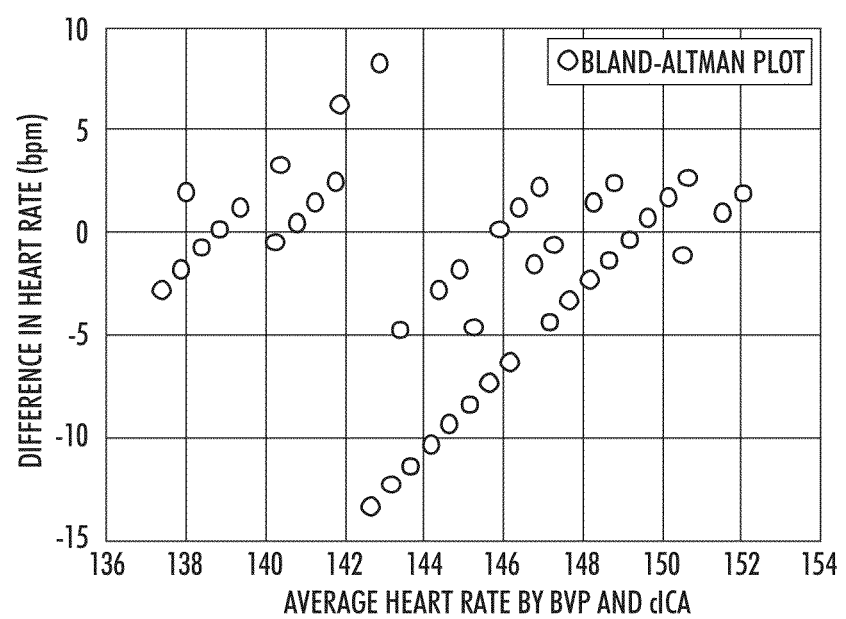
FIG. 15 shows Bland-Altman plots between estimated and true pulse using the present method (FIG. 13)

An example of monitoring pulse rate of an infant on a continuous basis is shown in FIGS. 12 and 13 wherein the ground truth recorded from FDA-approved Philips health monitoring system, at the time the video of the infant was captured, in beats per minute (bpm) is plotted against pulse estimated using the teachings hereof. FIG. 12 shows estimated and true pulse rate plotted against time using a prior art method and FIG. 13 shows the present method. It is observed that the tracking is not very exact since the algorithm suffers various artifacts but it does follow a trend, is more accurate than previous frequency sweep cICA algorithms, and is computationally efficient since the number of computation is reduced by a factor of about 120. Moreover, the pulse rate of infants is not stable even for a small duration of two-minutes and varies within a large range of 136-153 bpm. The agreement between all measurements was tested by a Bland-Altman plot with a standard deviation of 5.7 bpm (FIG. 14) and 8.9 bpm (FIG. 15) with respect to the prior art and the present method respectively. Clearly, there is an improvement over the method of the prior art.

Example Special Purpose Computer

Figure 16:
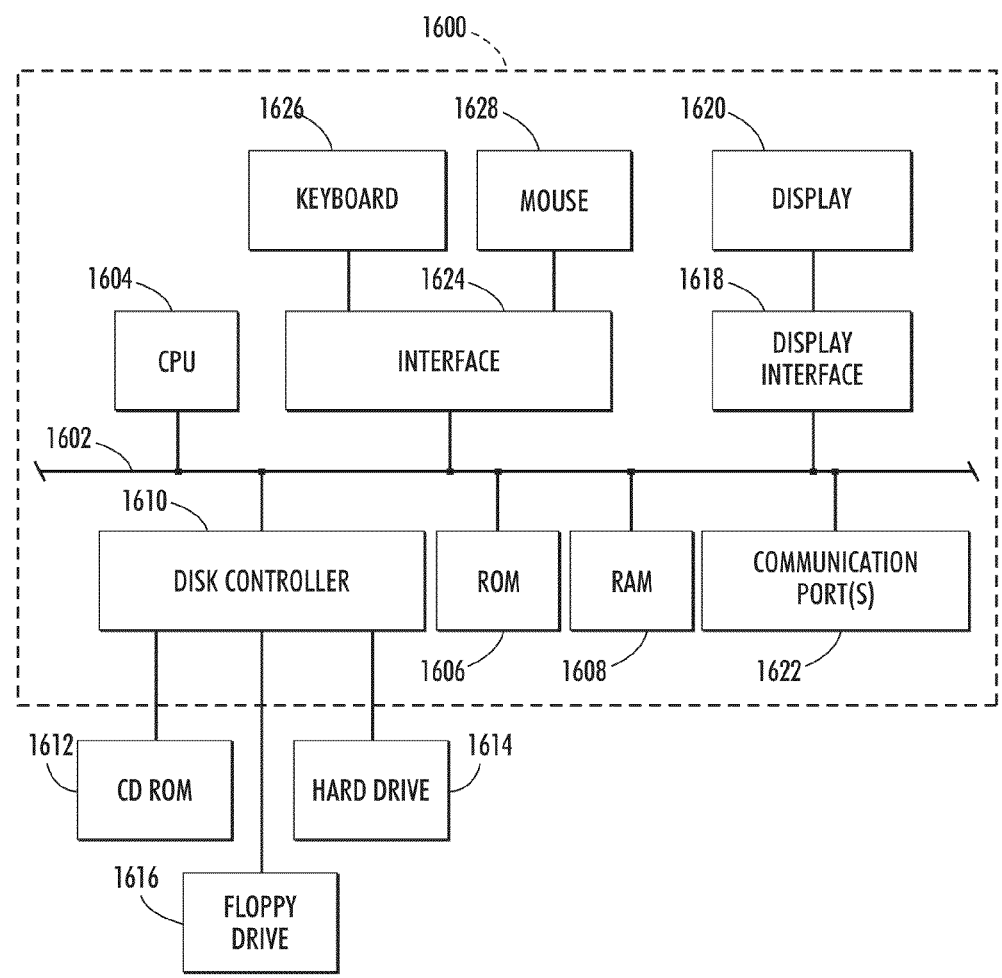
FIG. 16 illustrates a block diagram of one example special purpose computer for implementing one or more aspects of the present method as described with respect to the flow diagrams of FIGS. 4-6, and the block diagrams of FIGS. 3 and 8.

Reference is now being made to FIG. 16 which illustrates a block diagram of one example special purpose computer 1600 for implementing one or more aspects of the present method as described with respect to the flow diagrams of FIGS. 4-6, and the block diagrams of FIGS. 3 and 8. Such a special purpose processor is capable of executing machine executable program instructions and may comprise any of a micro-processor, micro-controller, ASIC, electronic circuit, or any combination thereof.

In FIG. 16, communications bus 1602 is in communication with a central processing unit (CPU) 1604 capable of executing machine readable program instructions for performing any of the calculations, comparisons, logical operations, and other program instructions for performing any of the steps described above with respect to the flow diagrams and the block diagrams hereof. Processor 1604 is in communication with memory (ROM) 1606 and memory (RAM) 1608 which, collectively, constitute example storage devices. Such memory may be used to store machine readable program instructions and other program data and results to sufficient to carry out any of the functionality described herein. Disk controller 1610 interfaces with one or more storage devices 1614 which may comprise external memory, zip drives, flash memory, USB drives, or other devices such as CD-ROM drive 1612 and floppy drive 1616. Storage device stores machine executable program instructions for executing the methods hereof. Such storage devices may be used to implement a database wherein various records are stored. Display interface 1618 effectuates the display of information on display 1620 in various formats such as, for instance, audio, graphic, text, and the like. Interface 1624 effectuates a communication via keyboard 1626 and mouse 1628, collectively a graphical user interface. Such a graphical user interface is useful for a user to enter information about any of the displayed information in accordance with various embodiments hereof. Communication with external devices may occur using example communication port(s) 1622. Such ports may be placed in communication with any of the example networks shown and described herein, such as the Internet or an intranet, either by direct (wired) link or wireless link. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

It will be appreciated that the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be included as part of an operating system, a plug-in, or may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for continuous cardiac pulse rate estimation from video images captured of a subject of interest being monitored for cardiac function, the method comprising:
   receiving a time-series signal of a subject of interest being monitored for cardiac function;
   overlaying said received time-series signal with a sliding window, said sliding window defining segments of said received time-series signal for processing, each successive position of said sliding window defining a next segment of said time-series signal for processing;
   defining a seed reference signal with a frequency range that approximates a frequency range of said subject's cardiac pulse; and
   processing segments of said received time-series signal by repeatedly:
      performing constrained source separation (cICA) on said signal segment using said seed reference signal to obtain an estimated source signal, said cICA converging on an occurrence of one of: an error between said estimated source signal and said seed reference signal being less than a threshold, and a pre-defined number of iterations having occurred;
      A) in response to said error being less than said threshold:
         determining a frequency of said estimated source signal as said subject's estimated cardiac pulse rate for this time-series signal segment;
         using said estimated source signal as said seed reference signal for processing a next time-series signal segment on a next iteration; and
         shifting said sliding window to define a next segment of said time-series signal, said next segment at least partially overlapping a previous time-series signal segment defined by said window on a last iteration; and
      B) in response to said pre-defined number of iterations having occurred, performing one of:
         updating said seed reference signal by changing any of: a frequency, an amplitude, a phase, and a waveform of said seed reference signal, and using said updated reference signal as said seed reference signal to re-process said time-series signal segment; and
         selecting an estimated source signal obtained from having processed a previous time-series signal segment and using said selected estimated source signal as said seed reference signal to re-process said time-series signal segment.

2. The method of claim 1, wherein said time-series signal is received on a continuous basis and processed as said time-series signal is being received.

3. The method of claim 1, wherein said received time-series signal comprises any of: RGB signals, IR signals, RGB and IR signals, multi-spectral signals, and hyperspectral signals.

4. The method of claim 1, wherein, in advance of using said estimated source signal as said seed reference signal, further comprising conditioning said estimated source signal to remove artifacts.

5. The method of claim 1, wherein said waveform comprises any of: a sine wave, a square wave, a user-defined shape obtained from an ECG signal, and a cardiac pulse waveform derived from said subject.

6. The method of claim 1, wherein said time-series signal comprises one of: stored values, and values generated from a streaming video.

7. The method of claim 1, wherein at least two of said time-series signal segments are defined by windows with a different size.

8. The method of claim 1, further comprising providing said subject's estimated cardiac pulse rate to a display device.

9. A system for continuous cardiac pulse rate estimation from video images captured of a subject of interest being monitored for cardiac function, the system comprising:
   a memory; and
   a processor in communication with said memory, said processor executing machine readable instructions for performing:
      receiving a time-series signal of a subject of interest being monitored for cardiac function;
      overlaying said received time-series signal with a sliding window, said sliding window defining segments of said received time-series signal for processing, each successive position of said sliding window defining a next segment of said time-series signal for processing;
      defining a seed reference signal with a frequency range that approximates a frequency range of said subject's cardiac pulse; and
      processing segments of said received time-series signal by repeatedly:
         performing constrained source separation (cICA) on said signal segment using said seed reference signal to obtain an estimated source signal, said cICA converging on an occurrence of one of: an error between said estimated source signal and said seed reference signal being less than a threshold, and a pre-defined number of iterations having occurred;
         A) in response to said error being less than said threshold:
            determining a frequency of said estimated source signal as said subject's estimated cardiac pulse rate for this time-series signal segment;
            using said estimated source signal as said seed reference signal for processing a next time-series signal segment on a next iteration; and shifting said sliding window to define a next segment of said time-series signal, said next segment at least partially overlapping a previous time-series signal segment defined by said window on a last iteration; and B) in response to said pre-defined number of iterations having occurred, performing one of:

updating said seed reference signal by changing any of: a frequency, an amplitude, a phase, and a waveform of said seed reference signal, and using said updated reference signal as said seed reference signal to re-process said time-series signal segment; and selecting an estimated source signal obtained from having processed a previous time-series signal segment and using said selected estimated source signal as said seed reference signal to re-process said time-series signal segment.

10. The system of claim 9, wherein said time-series signal is received on a continuous basis and processed as said time-series signal is being received.

11. The system of claim 9, wherein said received time-series signal comprises any of: RGB signals, IR signals, RGB and IR signals, multi-spectral signals, and hyperspectral signals.

12. The system of claim 9, wherein, in advance of using said estimated source signal as said seed reference signal, further comprising conditioning said estimated source signal to remove artifacts.

13. The system of claim 9, wherein said waveform comprises any of: a sine wave, a square wave, a user-defined shape obtained from an ECG signal, and a cardiac pulse waveform derived from said subject.

14. The system of claim 9, wherein at least two of said time-series signal segments are defined by windows with a different size.

15. The system of claim 9, wherein said time-series signal comprises one of: stored values, and values generated from a streaming video.

16. The system of claim 9, further comprising providing said subject's estimated cardiac pulse rate to a display device.

17. A non-transitory computer readable media containing machine readable program instructions for performing a method comprising: receiving a time-series signal of a subject of interest being monitored for cardiac function;

overlaying said received time-series signal with a sliding window, said sliding window defining segments of said received time-series signal for processing, each successive position of said sliding window defining a next segment of said time-series signal for processing;

defining a seed reference signal with a frequency range that approximates a frequency range of said subject's cardiac pulse; and processing segments of said received time-series signal by repeatedly:

performing constrained source separation (cICA) on said signal segment using said seed reference signal to obtain an estimated source signal, said cICA converging on an occurrence of one of: an error between said estimated source signal and said seed reference signal being less than a threshold, and a pre-defined number of iterations having occurred;

A) in response to said error being less than said threshold:

determining a frequency of said estimated source signal as said subject's estimated cardiac pulse rate for this time-series signal segment;

using said estimated source signal as said seed reference signal for processing a next time-series signal segment on a next iteration; and shifting said sliding window to define a next segment of said time-series signal, said next segment at least partially overlapping a previous time-series signal segment defined by said window on a last iteration; and B) in response to said pre-defined number of iterations having occurred, performing one of:

updating said seed reference signal by changing any of: a frequency, an amplitude, a phase, and a waveform of said seed reference signal, and using said updated reference signal as said seed reference signal to re-process said time-series signal segment; and selecting an estimated source signal obtained from having processed a previous time-series signal segment and using said selected estimated source signal as said seed reference signal to re-process said time-series signal segment.

18. The non-transitory computer readable media of claim 17, wherein said time-series signal is received on a continuous basis and processed as said time-series signal is being received.

19. The non-transitory computer readable media of claim 17, wherein said received time-series signal comprises any of: RGB signals, IR signals, RGB and IR signals, multi-spectral signals, and hyperspectral signals.

20. The non-transitory computer readable media of claim 17, wherein, in advance of using said estimated source signal as said seed reference signal, further comprising conditioning said estimated source signal to remove artifacts.

21. The non-transitory computer readable media of claim 17, wherein said waveform comprises any of: a sine wave, a square wave, a user-defined shape obtained from an ECG signal, and a cardiac pulse waveform derived from said subject.

22. The non-transitory computer readable media of claim 17, wherein said time-series signal comprises one of: stored values, and values generated from a streaming video.

23. The non-transitory computer readable media of claim 17, wherein at least two of said time-series signal segments are defined by windows with a different size.

24. The non-transitory computer readable media of claim 17, further comprising providing said subject's estimated cardiac pulse rate to a display device.

\* \* \* \* \*